United States Patent
Takakura et al.

(10) Patent No.: US 10,045,733 B2
(45) Date of Patent: Aug. 14, 2018

(54) SLEEP SENSOR

(71) Applicant: TDK Corporation, Minato-ku, Tokyo (JP)

(72) Inventors: Junya Takakura, Kanagawa (JP); Kanako Nakayama, Tokyo (JP); Yasunobu Yamauchi, Kanagawa (JP)

(73) Assignee: TDK CORPORATION, Tokyo (JP)

( * ) Notice: Subject to any disclaimer, the term of this patent is extended or adjusted under 35 U.S.C. 154(b) by 202 days.

(21) Appl. No.: 14/749,106

(22) Filed: Jun. 24, 2015

(65) Prior Publication Data

US 2015/0374284 A1 Dec. 31, 2015

(30) Foreign Application Priority Data

Jun. 25, 2014 (JP) .................................. 2014-130290

(51) Int. Cl.
*A61B 5/08* (2006.01)
*A61B 5/00* (2006.01)
(Continued)

(52) U.S. Cl.
CPC .......... *A61B 5/4818* (2013.01); *A61B 5/0826* (2013.01); *A61B 5/1116* (2013.01);
(Continued)

(58) Field of Classification Search
CPC ... A61B 5/4806; A61B 5/4818; A61B 5/7285; A61B 5/7278; A61B 5/1116;
(Continued)

(56) References Cited

U.S. PATENT DOCUMENTS

| | | | |
|---|---|---|---|
| 6,356,203 B1* | 3/2002 | Halleck | A61B 5/1117 200/61.45 R |
| 2009/0062628 A1* | 3/2009 | Yamamoto | A61B 5/08 600/301 |
| 2009/0062828 A1 | 3/2009 | Yamamoto et al. | |
| 2011/0066042 A1* | 3/2011 | Pandia | A61B 5/029 600/484 |

(Continued)

FOREIGN PATENT DOCUMENTS

| | | |
|---|---|---|
| JP | 2001-190503 A | 7/2001 |
| JP | 2006-247374 | 9/2006 |
| JP | 2013-236925 A | 11/2013 |

OTHER PUBLICATIONS

Richard, Wietske, et al. "The role of sleep position in obstructive sleep apnea syndrome." European Archives of Oto-Rhino-Laryngology and Head & Neck 263.10 (2006): 946-950.*

(Continued)

*Primary Examiner* — Navin Natnithithadha
*Assistant Examiner* — Andrey Shostak
(74) *Attorney, Agent, or Firm* — Oliff PLC (57) ABSTRACT

According to one embodiment, a sleep sensor which is attached to a user who is sleeping when it is to be used is provided. The sleep sensor includes a first detector, an estimation module, a second detector and a control module. The first detector is configured to detect an acceleration signal representing acceleration that is obtained from the sleep sensor. The estimation module is configured to estimate the user's body position based on the detected acceleration signal. The second detector is configured to detect a signal for estimating a state other than the user's body position. The control module is configured to operate the second detector when the estimated user's body position is at least one of predefined body positions.

1 Claim, 7 Drawing Sheets

(51) Int. Cl.
*A61B 5/11* (2006.01)
*A61B 7/00* (2006.01)

(52) U.S. Cl.
CPC .......... *A61B 5/6823* (2013.01); *A61B 5/7278* (2013.01); *A61B 5/7285* (2013.01); *A61B 7/003* (2013.01); *A61B 2560/0412* (2013.01); *A61B 2562/0204* (2013.01); *A61B 2562/0219* (2013.01)

(58) Field of Classification Search
CPC ... A61B 5/4815; A61B 5/6823; A61B 5/0205; A61B 5/0402; A61B 5/113; A61B 5/024; A61B 5/02055; A61B 5/08; A61B 5/0245; A61B 5/0826; A61B 7/003; A61B 2562/0204; A61B 2562/0219; A61B 2560/0412
See application file for complete search history.

(56) References Cited

U.S. PATENT DOCUMENTS

| | | | |
|---|---|---|---|
| 2011/0137209 A1* | 6/2011 | Lahiji | .................... A61B 7/026 600/586 |
| 2013/0281883 A1 | 10/2013 | Nishida | |

OTHER PUBLICATIONS

English-language extended European search report by the European Patent Office in counterpart foreign Application No. 15168923.9, dated Nov. 23, 2015, 7 pages.

\* cited by examiner

SLEEP SENSOR

CROSS-REFERENCE TO RELATED APPLICATIONS

This application is based upon and claims the benefit of priority from Japanese Patent Application No. 2014-130290, filed Jun. 25, 2014, the entire contents of which are incorporated herein by reference.

FIELD

Embodiments described herein relate generally to a sleep sensor for estimating a state of a user during sleep.

BACKGROUND

Generally, in order to carry out a diagnosis of sleep apnea syndrome, for example, the user's state during sleep (hereinafter referred to as a sleep state) is estimated by using a body position sensor or a snore sensor, etc.

In this case, the body position sensor is attached to, for example, the user's chest, and the snore sensor is attached to, for example, the user's throat. Sleeping with a plurality of sensors separately attached at different parts of the body is very troublesome for the user.

Hence, recently, a sleep sensor (device) including a plurality of sensors to be used for estimating the user's sleep state has been developed. According to such a sleep sensor, not only the user's body position and respiratory state during sleep, but also other conditions such electrocardiographic activity, pulse waves, and body temperature can be estimated. Also, since it becomes unnecessary to attach a plurality of sensors separately as mentioned above, the burden on the user can be reduced.

Incidentally, the above-mentioned sleep sensor is often driven, by power supplied from a battery. In this situation, the sleep sensor must be driven by power supplied from the battery alone for a long time in order to estimate the user's sleep state as described above.

However, since the power supplied from the battery is limited, a mechanism for achieving power-saving in order to realize long-time driving of the sleep sensor including a plurality of sensors is desired.

DETAILED DESCRIPTION

Various embodiments will be described hereinafter with reference to the accompanying drawings.

In general, according to one embodiment, a sleep sensor which is attached to a user who is sleeping when it is to be used is provided. The sleep sensor includes a first detector, an estimation module, a second detector and a control module. The first detector is configured to detect an acceleration signal representing acceleration that is obtained from the sleep sensor. The estimation module is configured to estimate the user's body position based on the detected acceleration signal. The second detector is configured to detect a signal for estimating a state other than the user's body position. The control module is configured to operate the second detector when the estimated user's body position is at least one of predefined body positions.

First Embodiment

Figure 1:
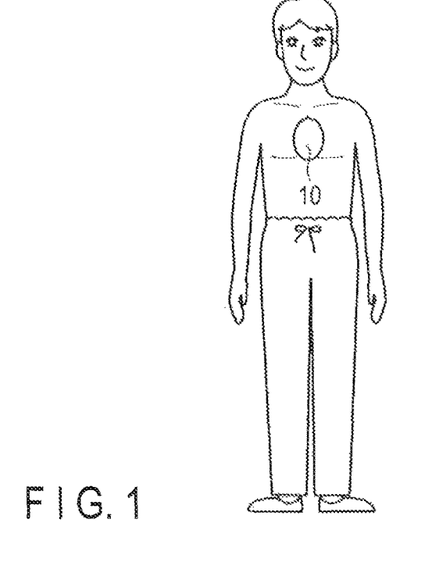
FIG. 1 is an illustration showing on example of usage of a sleep sensor according to a first embodiment.

FIG. 1 shows an example of usage of a sleep sensor (device) according to a first embodiment. A sleep sensor 10 shown in FIG. 1 is a small, light, and thin device which is used for estimating the user's state during sleep (which is hereinafter referred to as a sleep state). By using double-faced adhesive tape having adhesiveness or a gel pad, etc., an attachment surface of the sleep sensor 10 is stuck to the chest of the user who is sleeping when it is to be used. The sleep sensor 10 has a shape which is close to an oval or a rectangle, for example, to allow the sleep sensor 10 to be easily attached near the central part of the chest.

Note that the user's sleep state estimated by the sleep sensor 10 includes, for example, the user's body position (orientation or posture of the body), and respiratory state during sleep.

Figure 2:
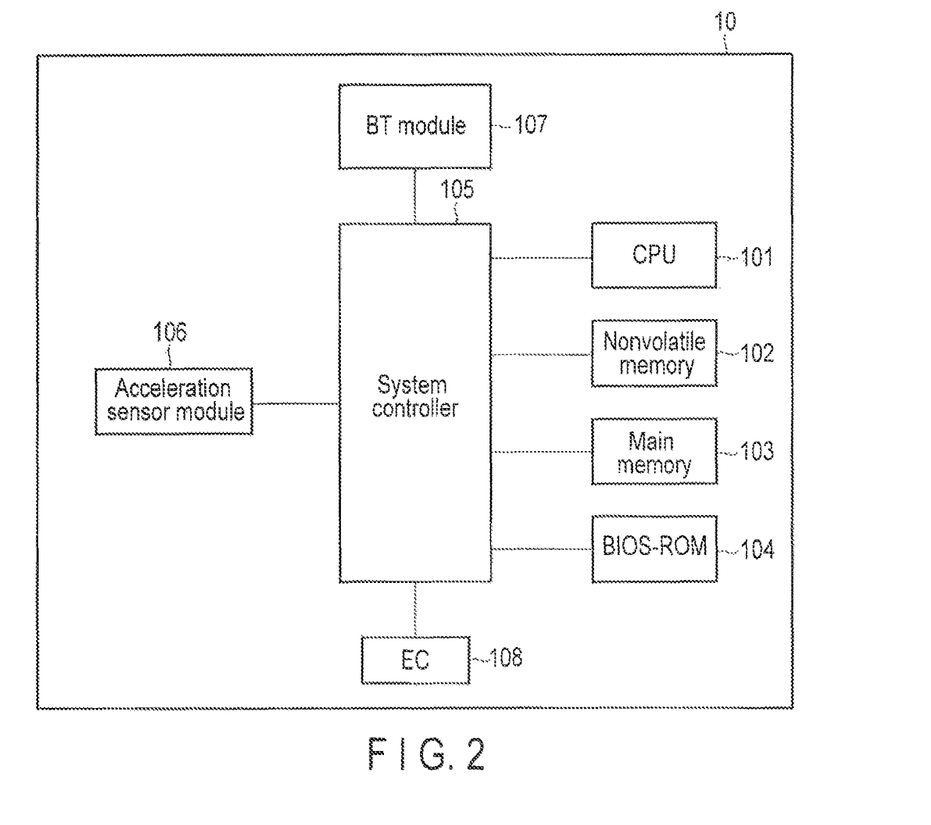
FIG. 2 is a diagram showing a system configuration of the sleep sensor shown in FIG. 1.

FIG. 2 is a diagram showing a system configuration of the sleep sensor 10 shown in FIG. 1. As shown in FIG. 2, the sleep sensor 10 includes a CPU 101, a nonvolatile memory 102, a main memory 103, a BIOS-ROM 104, a system controller 105, on acceleration sensor module 106, a BT module 107, an EC 108, etc.

The CPU 101 is a processor for controlling the operation of each component in the sleep sensor 10. The CPU 101 executes various kinds of software loaded into the main memory 103 from the nonvolatile memory 102, which is a storage device.

The CPU 101 executes a Basic Input/Output System (BIOS) stored in the BIOS-ROM 104. The BIOS is a program for hardware control.

The system controller 105 is a bridge device for connecting between the CPU 101 and each component. The CPU 101, the nonvolatile memory 102, the main memory 103, the BIOS-ROM 104, the acceleration sensor module 106, the BT module 107, the EC 108, etc. are connected to the system controller 105.

The acceleration sensor module 106 includes an acceleration sensor capable of sensing an acceleration signal, and is a module used for estimating the user's body position and respiratory state of during sleep. A configuration of the acceleration sensor module 106 will be described later.

The BT module 107 is a module configured to execute wireless communication with a Bluetooth-enabled device by using Bluetooth (registered trademark). The Bluetooth-enabled device includes, for example, a smartphone, a tablet computer, and a personal computer (PC).

The EC 108 is a power management controller for executing power management of the sleep sensor 10.

Note that several kinds of sensors capable of sensing, for example, the electrocardiographic activity, pulse waves, and body temperature may be provided in the sleep sensor 10 of the present embodiment, other than the above-mentioned acceleration sensor, although this is not illustrated in FIG. 2.

As can be seen, a plurality of sensors are provided within a single housing of the sleep sensor 10. Here, since analog front ends of the plurality of sensors have different specifications depending on the type of sensor, satisfying both the flexibility and high-performance is required, which may lead to an increase in size. However, in the present embodiment, since a plurality of analog front ends and the CPU 101, etc. are integrated on a single chip by using psuedo-SoC technology, a module of several millimeters square is realized. Note that the psuedo-SoC technology is one which satisfies both size reduction equivalent to an SoC and a degree of design freedom equivalent to an SiP by integrating parts on a wafer. By connecting an antenna and only a few peripheral parts such as a battery to the module, the sleep sensor 10 which is small, light (ten-odd grams or so), and thin (several millimeters or so) can be realized. Note that while it has been described size reduction of the sleep sensor 10 is realized by using the psuedo-SoC technology, the size reduction can also be realized by using an LSI, for example.

Figure 3:
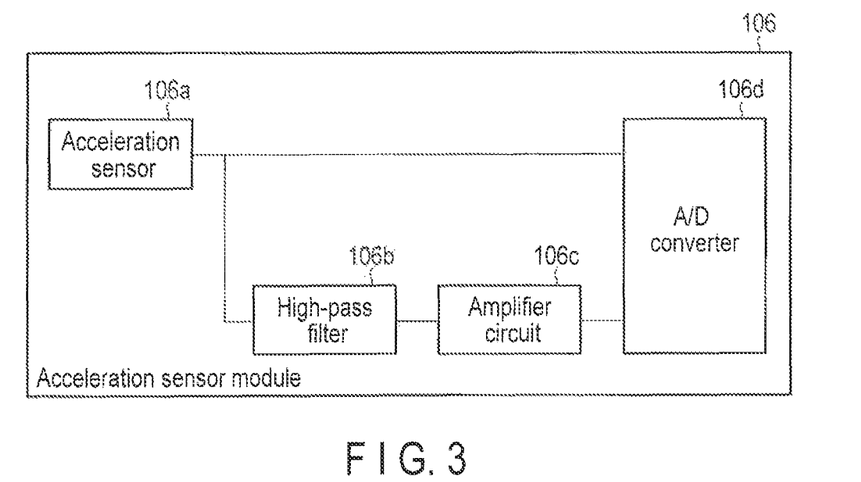
FIG. 3 is a diagram for describing a configuration of an acceleration sensor module shown in FIG. 2.

With reference to FIG. 3, the configuration of the acceleration sensor module 106 shown in FIG. 2 will be described. As shown in FIG. 3, the acceleration sensor module 106 includes an acceleration sensor 106a, a high-pass filter 106b, an amplifier circuit 106c, an A/D converter 106d, etc.

The acceleration sensor 106a is a sensor for sensing an acceleration signal representing acceleration that acts on the sleep sensor 10. It is assumed that the acceleration sensor 106a is a triaxial acceleration sensor (a three-dimensional acceleration sensor) capable of sensing the acceleration signal in each of the directions of, for example, three orthogonal axes (the x-axis, the y-axis, and the z-axis). Also, the acceleration signal sensed (output) by the acceleration sensor 106a are an analog signal.

Note that while the sleep sensor 10 has, for example, an oval shape as described above, (the acceleration signal produced in accordance with) an vibratory motion is sometimes hard to be sensed near the center of the sleep sensor 10. Accordingly, in order to more accurately sense the acceleration signal, the acceleration sensor 106a is arranged at a position which is deviated from the center of the sleep sensor 10, for example.

The high-pass filter 106b extracts an alternating-current component of the acceleration signal from the acceleration signal sensed by the acceleration sensor 106a.

The amplifier circuit (analog circuit) 106c amplifies the alternating-current component extracted by the high-pass filter 106b.

The A/D converter 106d converts the acceleration signal (an analog signal) sensed by the acceleration sensor 106a into a digital signal. Also, the A/D converter 106d converts the alternating-current component of the acceleration signal amplified by the amplifier circuit 106c into a digital signal.

Figure 4:
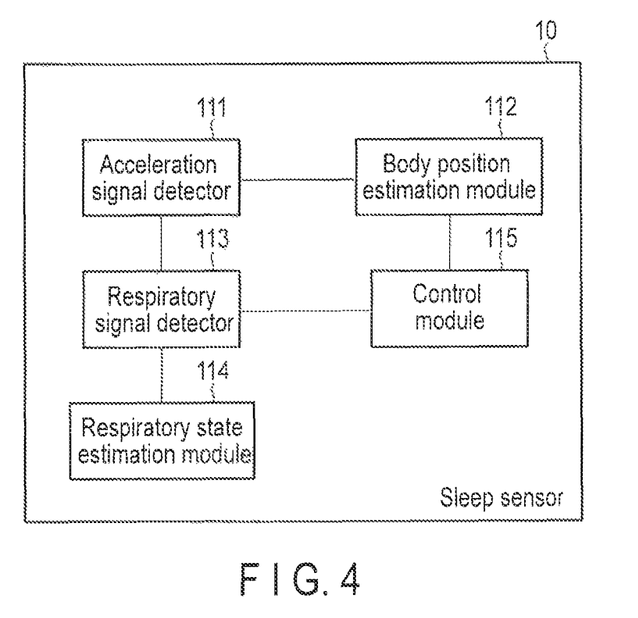
FIG. 4 is a block diagram showing mainly a functional configuration of the sleep sensor according to the present embodiment.

FIG. 4 is a block diagram showing mainly a functional configuration of the sleep sensor 10 according to the present embodiment. As shown in FIG. 4, the sleep sensor 10 includes an acceleration signal detector 111, a body position estimation module 112, a respiratory signal detector 113, a respiratory state estimation module 114, and a control module 115.

The acceleration signal detector 111 is a functional module which is realized by the acceleration sensor 106a described above, and detects the acceleration signal by using the acceleration sensor 106a. That is, the acceleration signal detector 111 detect an acceleration signal representing acceleration that is obtained from the sleep sensor 10. The acceleration signal detected by the acceleration signal detector 111 includes a direct-current component mainly representing gravitational acceleration, and an alternating-current component mainly representing acceleration which is produced by the user's state (for example, the respiratory state).

The body position estimation module 112 estimates the user's body position during sleep based on the acceleration signal detected by the acceleration signal detector 111. Note that the user's body position estimated by the body position estimation module 112 includes positions such as a supine position, a prone position, and a lateral position.

The respiratory signal detector 113 is a functional module which is realized by the high-pass filter 106b and the amplifier circuit 106c. The respiratory signal detector 113 cuts the direct-current component of the acceleration signal detected by the acceleration signal detector 111 in the high-pass filter 106b, and extracts the alternating-current component (a high-frequency component) of the acceleration signal. Also, the respiratory signal detector 113 amplifies the extracted alternating current component of the acceleration signal by using the amplifier circuit 106c. The respiratory signal detector 113 thereby detects the amplified alternating-current component of the acceleration signal as a signal for estimating the state ether than the user's body position (here, the user's respiratory state). In the following descriptions, the signal detected by the respiratory signal detector 113 (i.e., the amplified alternating-current component of the acceleration signal) will be referred to as a respiratory signal.

The respiratory state estimation module 114 estimates the user's respiratory state during sleep based on a respiratory signal detected by the respiratory signal detector 113. Note that the user's respiratory state estimated by the respiratory state estimation module 114 includes, for example, presence or absence of a symptom of snoring during sleep.

The control module 115 controls the operation of the respiratory signal detector 113. Specifically, the control module 115 executes the control to operate the respiratory signal detector 113 when the user's body position estimated by the body position estimation module 112 is at least one of predefined body positions (for example, the supine position, the prone position and so on).

The body position estimation module 112 and the respiratory state estimation module 114 are functional modules which are realized when the CPU 101 executes predetermined software (program). Further, the control module 115 is a functional module which is realized by, for example, the system controller 105.

Next, referring to the flowchart of FIG. 5, a processing procedure when the sleep sensor 10 according to the present embodiment estimates the user's sleep state (the body position and the respiratory state) will be described.

Firstly, the acceleration signal detector 111 detects an acceleration signal by using the acceleration sensor 106a (step S1). Note that the acceleration signal detected by the acceleration signal detector 111 is converted into a digital signal in the A/D converter 106d, and handed over to the body position estimation module 112.

The body position estimation module 112 estimates the user's body position during sleep based on the acceleration signal which has been converted into the digital signal in the A/D converter 106d (step S2).

Here, the estimation processing of the user's body position will be specifically described. Firstly, while the acceleration signal detected by the acceleration signal detector 111 includes a direct-current component (gravitational acceleration) and an alternating-current component (acceleration which is produced by the respiratory state, etc.) as described above, the acceleration sensor 106a in the present embodiment is a triaxial acceleration sensor. Accordingly, a direction of gravitational acceleration with respect to the sleep sensor 10 can be calculated from (the direct-current component of) the acceleration signal in each axial direction sensed by the acceleration sensor 106a. The user's body position is estimated based on the direction of the gravitational acceleration with respect to the sleep sensor 10 which has been thus calculated.

More specifically, with reference to the attachment surface of the sleep sensor 10, axes horizontal to the attachment surface and orthogonal to each other are defined as the x-axis and the y-axis, and an axis orthogonal to the x-axis and the y-axis (i.e., the axis normal to the attachment surface) is defined as the z-axis. When the sleep sensor 10 is attached to the user's chest, as shown in FIG. 1, the x-axis corresponds to a transverse axis relative, to the user's body (i.e., the direction of right and left of the body), the y-axis corresponds to a longitudinal axis relative to the user's body (i.e., the direction of head to toe of the body), and the z-axis corresponds to a front-to-back axis relative to the user.

In this case, when the direction of the gravitational acceleration with respect to the sleep sensor 10 is the back direction of the user in the z-axis (that is, backward to the user), it is estimated that the user's body position is the supine position. Meanwhile, when the direction of the gravitational acceleration with respect to the sleep sensor 10 is the front direction of the user in the z-axis (that is, forward to the user), it is estimated that the user's body position is the prone position. Also, when the direction of the gravitational acceleration with respect to the sleep sensor 10 is the x-direction (that is, right or left to the user), it is estimated that the user's body position is the lateral position.

When the user's body position is estimated in the above-described step S2, it is determined whether the user's body position, which has been estimated is the supine position (step S3).

When it has been determined that the user's body position is the supine position (YES in step S3), the control module 115 executes the control of starting the operation of the respiratory signal, detector 113 (step S4). In this case, the control module 115 powers on the respiratory signal detector 113 (that is, the high-pass filter 106b and the amplifier circuit 106c). Accordingly, the respiratory signal detector 113 is able to detect a respiratory signal.

In this case, the respiratory signal detector 113 extracts, from the acceleration signal detected by the acceleration signal detector 111 in step S1, an alternating-current component of the acceleration signal, by using the high-pass filter 106b (step S5).

Here, the A/D converter 106d according to the present embodiment needs to perform A/D conversion for both of (the direct-current component of) the acceleration signal detected by the acceleration signal detector 111 and the alternating-current component of the acceleration signal, in order so estimate the user's body position and respiratory state. In this case, the amplitude of the alternating-current component of the acceleration signal is extremely small as compared to that of the acceleration signal. More specifically, while detecting an acceleration signal within the range of ±1 G is necessary to estimate the body position, the magnitude of the alternating-current component of the acceleration signal detected for estimating the respiratory state is, for example, several milliG or less. In contrast, a resolution of the A/D converter 106d which can be mounted on the sleep sensor 10 is generally 8 to 12 bits or so, for example.

That is, the alternating-current component of the acceleration signal extracted by using the high-pass filter 106b cannot be processed by the A/D converter 106d as it is. Hence, the respiratory signal detector 113 amplifies the extracted alternating-current component, of the acceleration signal by using the amplifier circuit 106c (step S6). An amplification rate of the alternating-current component of the acceleration signal in this case is assumed to be adjusted in accordance with a dynamic range of the A/D converter 106d such that the alternating-current component can be processed even by the resolution of the A/D converter 106d.

The alternating-current component of the acceleration signal amplified by the respiratory signal detector 113 (that is, the respiratory signal detected by the respiratory signal detector 113) is converted into a digital signal by the A/D converter 106d, and handed over to the respiratory state estimation module 114.

The respiratory state estimation module 114 estimates presence or absence of a symptom of snoring, for example, as the user's respiratory state during sleep, on the basis of the respiratory signal converted into the digital signal in the A/D converter 106d (step S7). In this case, the respiratory state estimation module 114 estimates the presence or absence of a symptom of snoring based on a feature amount calculated on the basis of, for example, the respiratory signal.

Meanwhile, when it is determined that the user's body position is not the supine position in the above step S3 (NO in step S3), the control module 115 executes the control of stopping the operation of the respiratory signal detector 113 (step S8). In this case, the control module 115 turns off power of the respiratory signal detector 113 (that is, the high-pass filter 106b and the amplifier circuit 106c). When this is carried out, since the respiratory signal detector 113 cannot detect a respiratory signal, the processing of the sleep sensor 10 is terminated.

It should be noted that the result of estimation of the user's body position in the above step S2, and the result of estimation of the user's respiratory state in step S7 are transmitted to an external Bluetooth-enabled device (a smartphone, a tablet computer, a PC, etc.) via the above-described BT module 107, and provided (presented) to a user, for example.

Note that while it has been described that each result of estimation is transmitted to a Bluetooth-enabled device, it is possible to adopt a structure in which the result of estimation is transmitted to an external server apparatus, etc., which functions as a cloud server that provides, for example, cloud computing service via a wireless LAN, etc., and stored in the server apparatus. Also, the result of estimation may be stored within the sleep sensor 10.

As described above, in the present embodiment, an acceleration signal representing acceleration that is obtained from the sleep sensor 10 is detected, and the user's body position is estimated based on the detected acceleration signal (gravitational acceleration). Further, in the present embodiment, a respiratory signal (an alternating-current component of the acceleration signal) is detected from the detected acceleration signal, and the user's respiratory state (presence or absence of a symptom of snoring) is estimated based on the detected respiratory signal. Also, in the present embodiment, the control to operate the respiratory signal detector 113 is executed when the estimated user's body position is a predefined body position (for example, the supine position). That is, in the present embodiment, control on a detection operation of a signal for estimating other states can be varied in accordance with a result of estimation of the user's body position.

Consequently, in the present embodiment, since she respiratory signal is detected (that is, the user's respiratory state is estimated) only when the user's body position is the supine position in terms of the fact that, for example, snoring is likely to occur in the supine position, it becomes possible to reduce the power consumption (that is, achieve power saving) when the user's body position is a position other than the supine position.

Also, in the present embodiment, since the user's respiratory state is estimated by using the alternating-current component extracted from the acceleration signal detected by the acceleration signal detector 111, it is unnecessary so provide, a sensor for estimating the user's body position and that for estimating the respiratory state separately. Thus, the sleep sensor 10 can be made small, light and thin in the present embodiment.

Further, in the present embodiment, since processing can be performed appropriately even by the A/D converter 106d of low resolution as the alternating-current component extracted from the acceleration signal detected by the acceleration signal detector 111 is amplified, there is no need to use an expensive A/D converter 106d and cost reduction can be realized.

Although it has been described that in the present embodiment, the respiratory signal detector 113 is operated when the user's body position is the supine position in terms of the fact that snoring is likely to occur in the supine position, a structure in which the respiratory signal detector 113 is operated in a predefined body position other than the supine position, for example, can also be adopted.

In addition, although it has been mainly described that the sleep sensor 10 is attached to the user's chest in the present embodiment, the sleep sensor 10 may be attached to other parts of the body as long as the user's body position and the respiratory state during sleep can be estimated by using the acceleration signal sensed by the acceleration sensor 106a, for example.

Further, although it has been described that the sleep sensor 10 includes the body position estimation module 112 and the respiratory state estimation module 114 in the present embodiment, a structure in which processing executed by the body position estimation module 112 and the respiratory state estimation module 114 is executed by, for example, an external Bluetooth-enabled device or a server apparatus, etc. can also be adopted.

Furthermore, means for communicating with the outside may be a wireless communication system other than Bluetooth, and the sleep sensor 10 may be a structure capable of storing data in a memory installed inside the sleep sensor 10 and outputting data after completion of the measurement by means such as USB.

Second Embodiment

Next, a second embodiment will be described. The point that a microphone is used for estimating the user's respiratory state (presence or absence of a symptom of snoring) in the present embodiment is different from the first embodiment described above.

Figure 6:
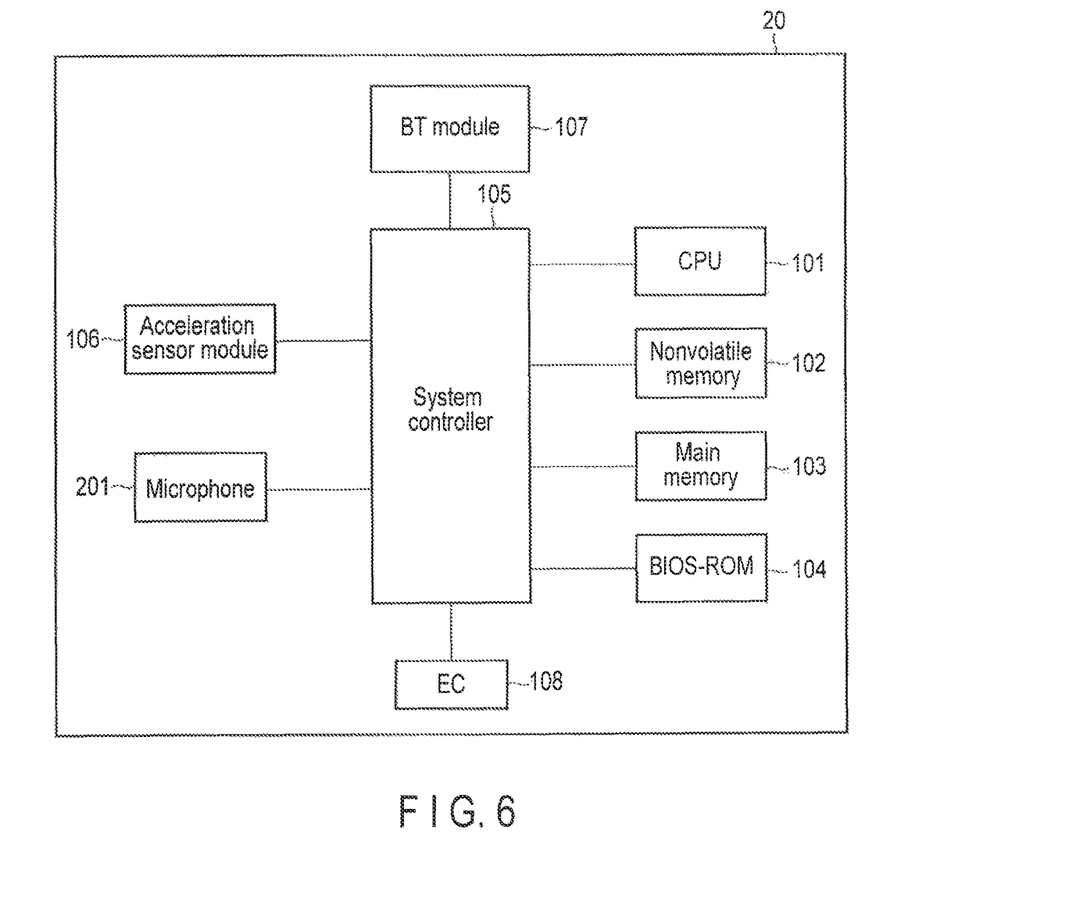
FIG. 6 is a diagram showing a system configuration of a sleep sensor according to a second embodiment.

FIG. 6 is a diagram showing a system configuration of a sleep sensor 20 according to the present embodiment. In FIG. 6, the same reference numbers are assigned to parts which are similar to those in FIG. 2 described above, and detailed explanation of them are omitted. Here, parts which are different from the configuration shown in FIG. 2 will be mainly described. Further, since usage of the sleep sensor 20 according to the present embodiment is as described with reference to FIG. 1 above, detailed explanation of the usage will be omitted.

As shown in FIG. 6, the sleep sensor 20 further includes a microphone 201 in addition to the system configuration of the above-described first embodiment.

The microphone 201 is used for estimating a respiratory state of the user during sleep, and senses a sound signal generated in accordance with the user's respiratory state. With the use of the microphone 201, a sound around the sleep sensor 20 can be converted into an electrical signal (a sound signal).

Figure 7:
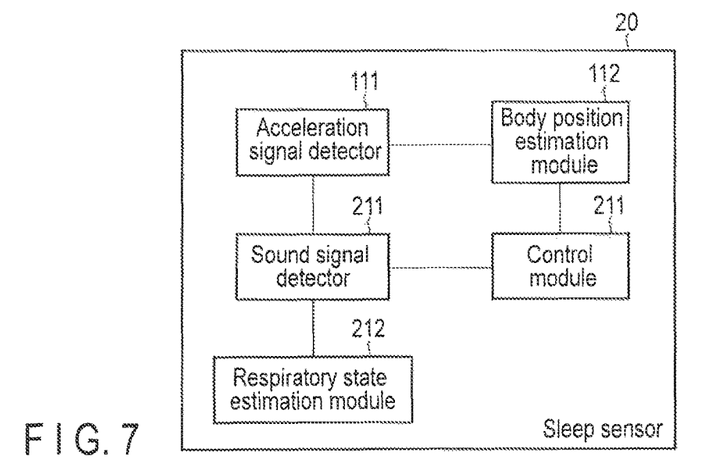
FIG. 7 is a block diagram showing mainly a functional configuration of the sleep sensor according to the present embodiment.

FIG. 7 is a block diagram showing mainly a functional configuration of the sleep sensor 20 according to the present embodiment. In FIG. 7, the same reference numbers are assigned to parts which are the same as those in FIG. 4 described above, and detailed explanation of them are omitted. Here, parts which are different from the configuration shown in FIG. 4 will be mainly described.

As shown in FIG. 7, the sleep sensor 20 includes a sound signal detector 211, a respiratory state estimation module 212, and a control module 213, in addition to the acceleration signal detector 111 and the body position estimation module 112 of the first embodiment described above.

The sound signal detector 211 is a functional module which is realized by the microphone 201 described above, and detects the sound signal by using the microphone 201. The sound signal detected by the sound signal detector 211 includes, for example, a signal of a respiratory sound, etc., which is generated by the user's symptom of snoring during sleep (hereinafter referred to as a snore signal), as the sound signal generated in accordance with the user's respiratory state.

The respiratory state estimation module 212 estimates the user's respiratory state during sleep based on the sound signal detected by the sound signal detector 211. The user's respiratory state estimated by the respiratory state estimation module 212 includes, for example, presence or absence of a symptom of snoring during sleep.

The control module 213 controls the operation of the sound signal detector 211. Specifically, the control module 213 executes the control to operate the sound signal detector 211 when the user's body position estimated by the body position estimation module 112 is a predefined body position (for example, the supine position).

The respiratory state estimation module 212 is a functional module which is realized when the above mentioned CPU 101 executes predetermined software (program). Further, the control module 213 is a functional module which is realized by, for example, a system controller 10.

Figure 8:
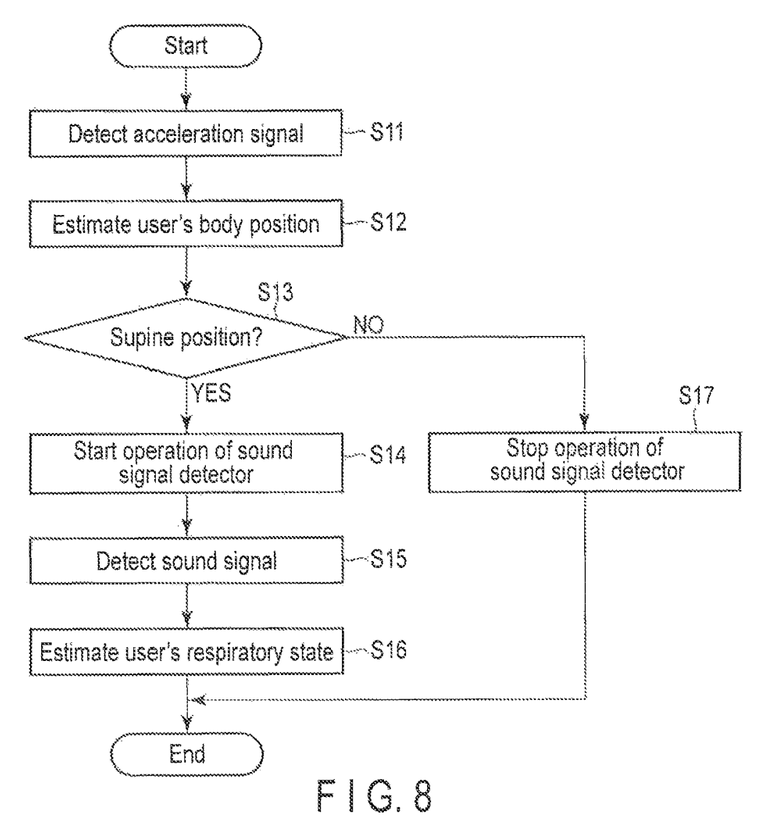
FIG. 8 is a flowchart showing a processing procedure when the sleep sensor according to the present embodiment estimates the user's sleep state.

Next, referring to the flowchart of FIG. 8, a processing procedure when the sleep sensor 20 according to the present embodiment estimates the user's sleep state the body position and the respiratory state) will be described.

Figure 5:
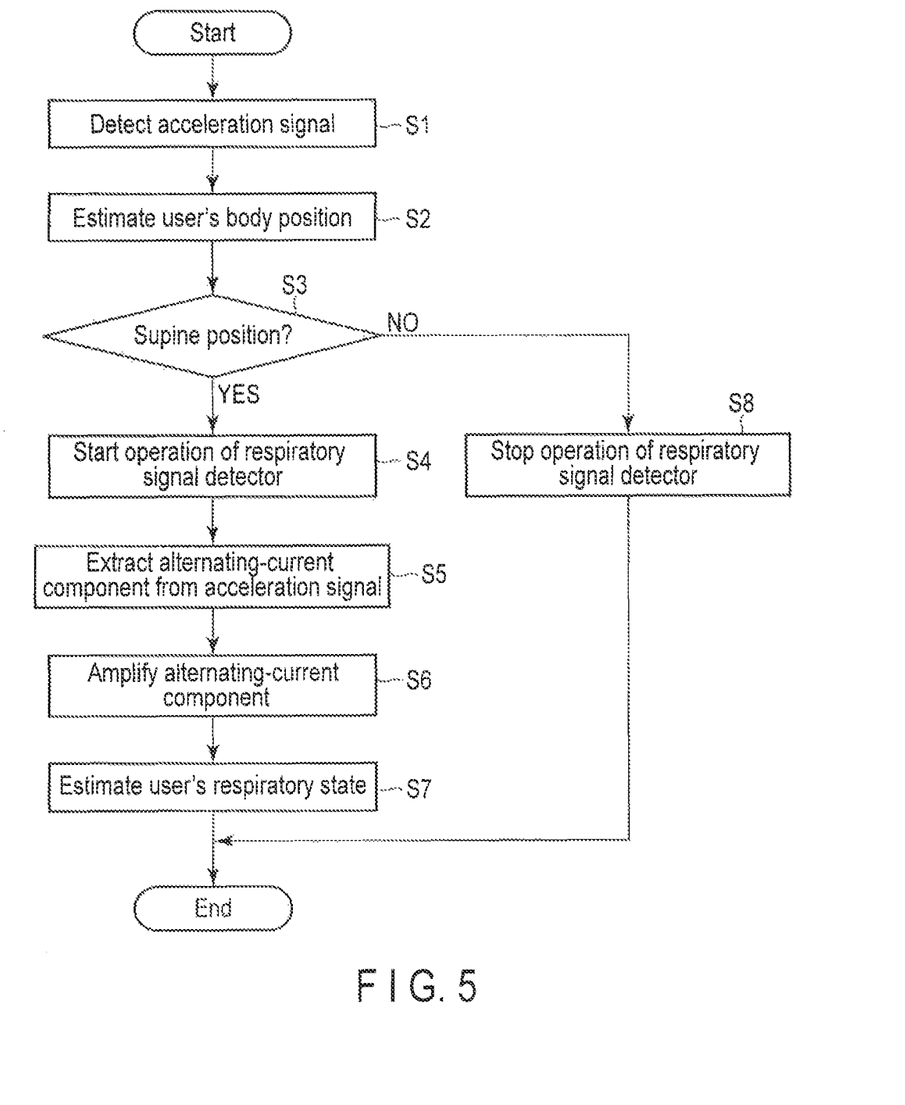
FIG. 5 is a flowchart showing a processing procedure when the sleep sensor according to the present embodiment estimates the user's sleep state.

First of all, processing of steps S11 to S13 corresponding to the processing of steps S1 to S3 shown in FIG. 5 described above is executed.

In step S13, when it is determined that the user's body position is the supine position (YES in step S13), the control module 213 executes the control of starting the operation of the sound signal detector 211 (step S14). In this case, the control module 213 powers on the sound signal detector 211 (that is, the microphone 201). Accordingly, the sound signal detector 211 is able to detect a sound signal.

In this case, by using the microphone 201, the sound signal detector 211 detects the sound signal representing a sound around the sleep sensor 20 (step S15).

Next, the respiratory state estimation module 212 estimates presence or absence of a symptom of snoring, for example, as the user's respiratory state during sleep, on the basis of the sound signal detected by the sound signal detector 211 (step S16). In this case, when the respiratory state estimation module 212 determines that the sound signal includes the aforementioned snore signal as a result of analyzing she sound signal detected by the sound signal detector 211, the respiratory state estimation module 212 can determine that the user shows the symptom of snoring.

Meanwhile, when it is determined that the user's body position is not the supine position so the above step S13 (NO in step S13), the control module 213 executes the control of stepping the operation of the sound signal detector 211 (step S17). In this case, the control module 213 powers off the sound signal detector 211 (that is the microphone 201). When this is carried out, since the sound signal, detector 211 cannot detect a sound signal, the processing of the sleep sensor 20 is terminated.

It should be noted that the result of estimation of the user's body position in the above step S12, and the result of estimation of the user's respiratory state in step S16 are transmitted to, for example, an external Bluetooth-enabled device or a server apparatus, etc., as in the first embodiment described above.

As described above, in the present embodiment, the control to operate the sound signal detector 211 is executed when the estimated user's body position is a predefined body position (for example, the supine position). In the present embodiment, by this structure, since the sound signal is detected (that is, the user's respiratory state is estimated) only when the user's body position is the supine position as in the first embodiment described above, it becomes possible to reduce the power consumption when the user's body position is not the supine position.

Note that in the present embodiment, since the acceleration signal is used for only estimating the user's body position and there is no need to extract an alternating-current component from the acceleration signal, a structure in which an acceleration sensor module 106 does not include a high-pass filter 106b and an amplifier circuit 106c may be adopted. Also, in the above first embodiment, it has been described that the acceleration sensor 106a outputs an analog signal. However, as long as the acceleration sensor 106a enables the user's body position to be estimated, the acceleration sensor 106a of the present embodiment may output a digital signal.

Further, although it has been described that the sound signal detector 211 is operated when the user's body position is the supine position in the present embodiment, a structure in which the sound signal detector 211 is operated in a predefined body position other than the supine position, for example, can also be adopted.

Furthermore, although it has been described that an attachment surface of the sleep sensor 20 is adhered to the user's chest in its use in the present embodiment, as long as the user's body position during sleep can be estimated by using the acceleration signal sensed by the acceleration sensor 106a, for example, and the user's respiratory state during sleep can be estimated by using the sound signal sensed by the microphone 201, the sleep sensor 20 may be attached to other parts of the body.

Moreover, although it has been described that the sleep sensor 20 includes the body position estimation module 112 and the respiratory state estimation module 212 in the present embodiment, a structure in which processing executed by the body position estimation module 112 and the respiratory state estimation module 212 is executed by, for example, an external Bluetooth-enabled device or a server apparatus, etc. can also be adopted.

Third Embodiment

Next, a third embodiment will, be described. In the present embodiment, the point that a microphone is used for estimating the user's respiratory state is the same as the second embodiment. However, the point that the microphone has directivity to a predetermined direction (high sound collecting capability) is different from the second embodiment described above. Since the system configuration of a sleep sensor according to the present embodiment is similar to that of the above-described second embodiment, explanation will be given by referring to FIG. 6 as necessary.

Figure 9:
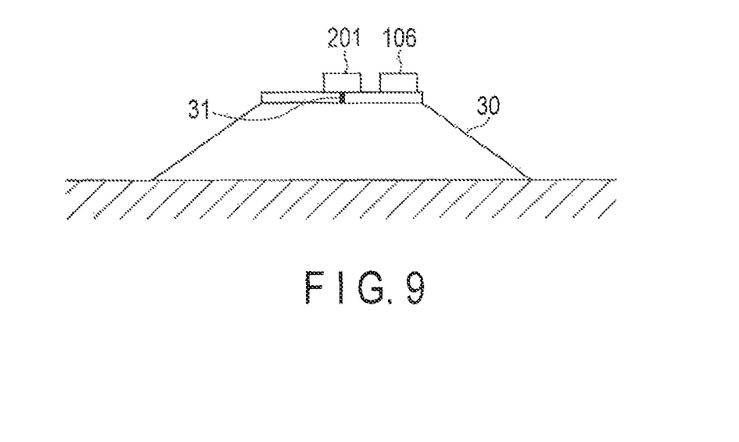
FIG. 9 is an illustration for describing the shape of a sleep sensor according to a third embodiment.

FIG. 9 is an illustration for describing the shape of a sleep sensor 30 according to the present embodiment. Note that the sleep sensor 30 according to the present embodiment is used by having an attachment surface of the sleep sensor 30 adhered to the user's chest, etc., as in the case of the first and second embodiments described above.

As shown in FIG. 9, in the present embodiment, the sleep sensor 30 includes a housing in the shape of stethoscope for example, and an acceleration sensor module 106 and a microphone 201 are arranged on the housing. Also, in this housing, a hole 31 is provided at a place where the microphone 201 is arranged in the direction of the attachment surface of the sleep sensor 30. In the present embodiment, because of such hole 31, the microphone 201 has directivity to the side of the attachment surface (that is, toward the interior of the user's body when the sleep sensor 30 is attached to the user). Further, as the microphone 201 of the present embodiment, an MEMS microphone or the like is used. Also, the microphone 201 (and the acceleration sensor module 106) is to be covered by a cover member or the like in order to reduce the influence of a sound, etc. around the sleep sensor 30, although this is not illustrated in FIG. 9. Further, instead of providing a hole as shown in FIG. 9, the microphone 201 may be mounted inside the mortar configuration.

Figure 10:
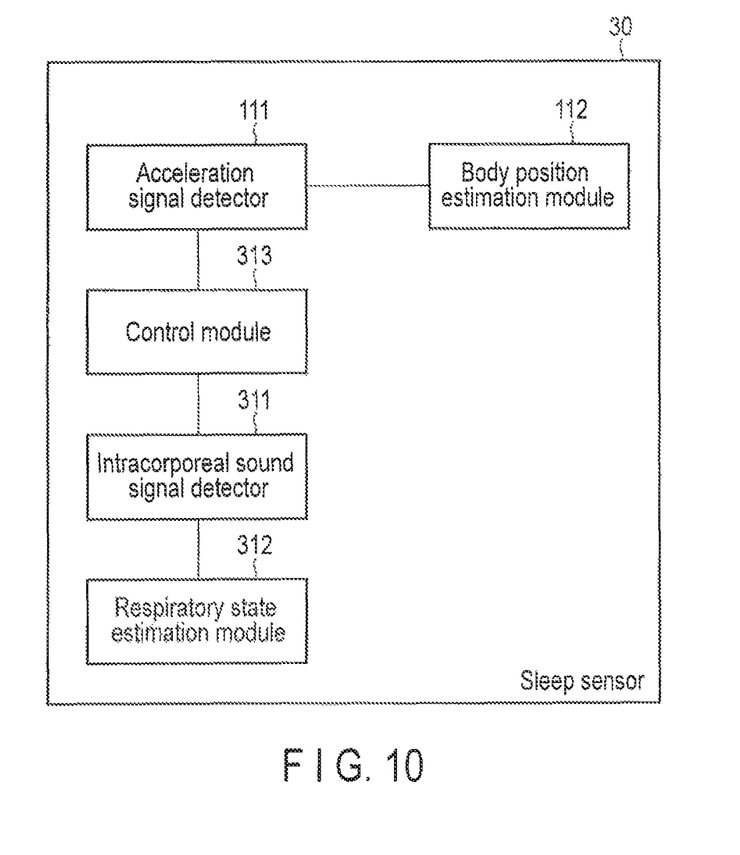
FIG. 10 is a block diagram showing mainly a functional configuration of the sleep sensor accordion to the present embodiment.

FIG. 10 is a block diagram showing mainly a functional configuration of the sleep sensor 30 according to the present embodiment. In FIG. 10, the same reference numbers are assigned to parts which are the same as those in FIGS. 4 and 7 described above, and detailed explanation of them are omitted. Here, parts which are different from the configuration shown in FIGS. 4 and 7 will be mainly described.

As shown in FIG. 10, the sleep sensor 30 includes an intracorporeal sounds signal detector 311, a respiratory state estimation module 312, and a control module 313, in addition to the acceleration signal detector 111 and the body position estimation module 112 of the first and the second embodiments described above.

The intracorporeal sound signal detector 311 is a functional module which is realized by the microphone 201, and detects a sound signal, by using the microphone 201. Further, since the microphone 201 of the present embodiment has directivity as described above, a sound signal detected by the intracorporeal sound signal detector 311 is an intracorporeal sound signal representing the user's intracorporeal sound.

The respiratory state estimation module 312 estimates the user's respiratory state during sleep based on the intracorporeal sound signal detected by the intracorporeal sound signal detector 311. The user's respiratory state estimated by the respiratory state estimation module 312 includes, for example, presence or absence of a symptom of snoring during sleep.

The control module 313 controls the operation of the sound signal detector 311. Specifically, the control module 313 executes the control to operate the intracorporeal sound signal detector 311 when the direction of gravitational acceleration calculated from an acceleration signal detected by the acceleration signal detector 111 agrees with the directivity of the microphone 201.

Note that the respiratory state estimation module 312 is a functional module which is realized when the above-mentioned CPU 101 executes predetermined software (program). Further, the control module 313 is a functional module which is realized by, for example, a system controller 105.

Figure 11:
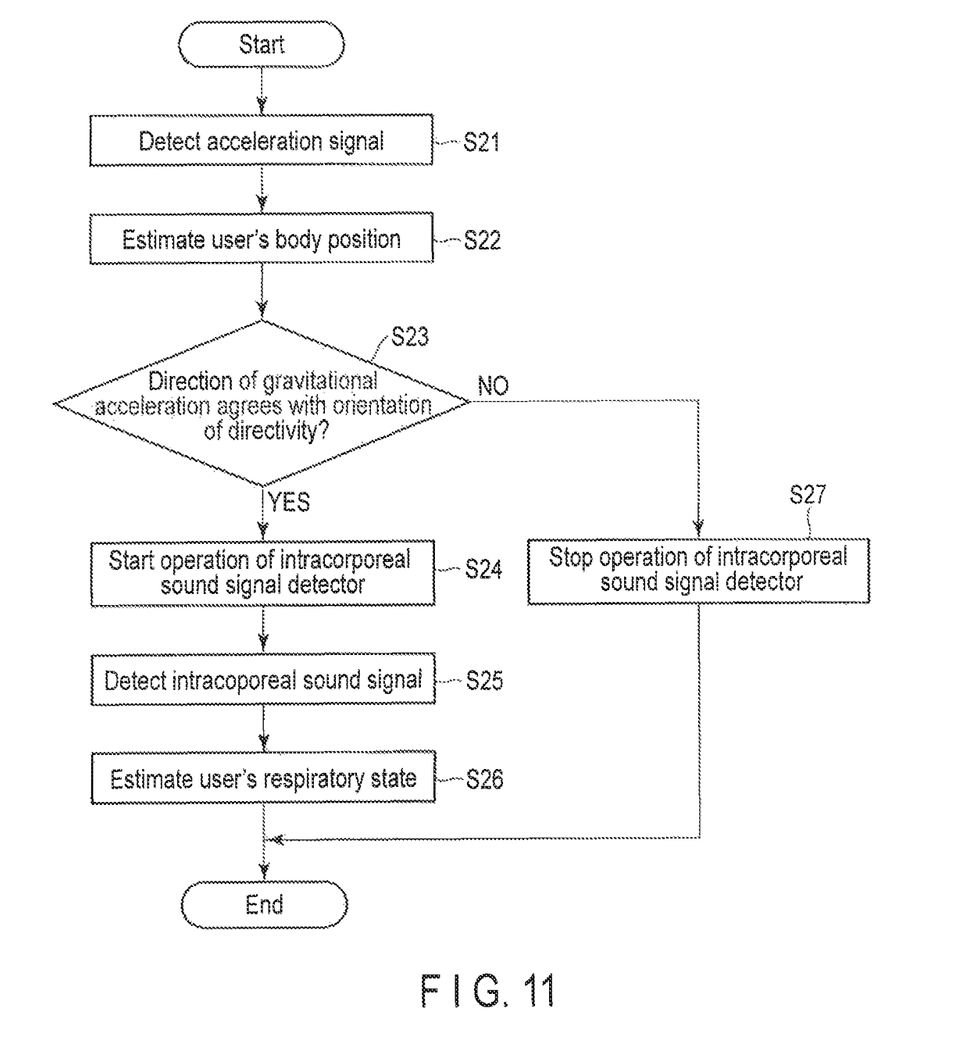
FIG. 11 is a flowchart showing a processing procedure when the sleep sensor according to the present embodiment estimates the user's sleep state.

Next, referring to the flowchart of FIG. 11, a processing procedure when the sleep sensor 30 according to the present embodiment estimates the user's sleep state the body position and the respiratory state) will be described.

First of all, processing of steps S21 and S22 corresponding to the processing of steps S1 and S2 shown in FIG. 5 described above is executed.

Next, it is determined whether the direction of gravitational acceleration in the user's body position estimated in step S22 agrees with the orientation of directivity of the microphone 201 (step S23).

When it is determined that the direction of gravitational acceleration agrees will the orientation of directivity of the microphone 201 (YES in step S23), the control module 313 executes the control of starting the operation of the intracorporeal sound signal detector 311 (step S24). In this case, the control module 313 powers on the intracorporeal sound signal detector 311 (that is, the microphone 201). Accordingly, the intracorporeal sound signal, detector 311 is able to detect an intracorporeal sound signal.

In this case, by using the microphone 201, the intracorporeal sound signal detector 311 detects the intracorporeal sound signal representing the user's intracorporeal sound (step S25).

Next, the respiratory state estimation module 312 estimates presence or absence of a symptom of snoring, for example, as the user's respiratory state during sleep, on the basis of the intracorporeal sound signal detected by the intracorporeal sound signal detector 311 (step S26). In this case, an intracorporeal sound signal, etc., when snoring occurs, for example, is stored in the sleep sensor 30 in advance, and by comparing the stored intracorporeal sound signal with the intracorporeal sound signal detected by the intracorporeal sound signal detector 311, whether or not the user shows a symptom of snoring can be estimated.

Meanwhile, when it is determined that the direction of gravitational acceleration does not agree with the orientation of directivity of the microphone 201 in step S23 (NO in step S23), the control module 313 executes the control of stopping the operation of the intracorporeal sound signal detector 311 (step S27). In this case, the control module 313 powers off the intracorporeal sound signal detector 311 (that is, the microphone 201). When this is carried out, since the intracorporeal sound signal detector 311 cannot detect an intracorporeal sound signal, the processing of the sleep sensor 30 is terminated.

It should be noted that the result of estimation of the user's body position in the above step S22, and the result of estimation of the user's respiratory state in step S25 are transmitted to, for example, an external Bluetooth-enabled device or a server apparatus, etc., as in the first and the second embodiments described above.

As described above, in the present embodiment, when the direction of gravitational acceleration that acts on the sleep sensor 30 agrees with the orientation of directivity of the microphone 201, the control to operate the intracorporeal sound signal detector 311 is executed.

Here, in order to accurately detect an intracorporeal sound signal, it is important that the microphone 201 be brought into close contact with the user's body surface. Therefore, in the present embodiment, an intracorporeal sound signal is detected (i.e., the user's respiratory state is estimated) only when the direction of gravitational acceleration that acts on the sleep sensor 30 agrees with the directivity of the microphone 201 (that is, the direction toward the interior of the user's body), in other words, the sleep sensor 30 is closely adhered to the user's body surface by its own weight. In this way, it is possible to accurately detect an intracorporeal sound signal, and also reduce the power consumption in a case where the sleep sensor 30 is not closely adhered to the body surface and the intracorporeal sound cannot be detected accurately.

Also, since the user's intracorporeal sound signal in the present embodiment is hard to be subjected to the influence of disturbance as compared to a sound signal around the sleep sensor 20 of the second embodiment described above, it becomes possible to more accurately estimate the user's respiratory state.

In the present embodiment, it has been described that the control to detect an intracorporeal sound signal is executed when the direction of gravitational acceleration that acts on the sleep sensor 30 agrees with the directivity of the microphone 201. However, a structure of executing the control, to detect an intracorporeal sound signal when the user's body position is the supine position may also be adopted, as described in the above, first and second embodiments.

Further, when the sleep sensor 30 is attached to the user's chest as described above, the user's body position when the direction of gravitational acceleration that acts on the sleep sensor 30 agrees with the directivity of the microphone 201 is often the supine position (face-up posture). Accordingly, also in the present embodiment, an intracorporeal sound signal is detected when the user's body position is the supine position (that is, a body position in which snoring is likely to occur) as a consequence.

Also, since there is no need to extract an alternating-current component from an acceleration signal in the present embodiment, as in the second embodiment described above, a structure in which an acceleration sensor module 106 does not include, a high-pass filter 106b and an amplifier circuit 106c may be adopted. Further, an acceleration sensor 106a of the present embodiment may be one which outputs an analog signal or one which outputs a digital signal as in the second embodiment described above.

In addition, although it has been described that an attachment surface of the sleep sensor 30 is adhered to the user's chest in its use in the present embodiment, as long as, for example, the user's body position during sleep can be estimated by using the acceleration signal sensed by the acceleration sensor 106a and the user's respiratory state during sleep can be estimated by using the intracorporeal sound signal sensed by the microphone 201, the sleep sensor 30 may be attached to other parts of the body.

Further, although it has been described that the sleep sensor 30 includes the body position estimation module 112 and the respiratory state estimation module 312 in the present embodiment, a structure in which processing executed by the body position estimation module 112 and the respiratory state estimation module 312 is executed by for example, an external Bluetooth-enabled device or a server apparatus, etc. can also be adopted.

Furthermore, in each of the above-described embodiments, it has been described that the user's respiratory state as the state other than the user's body position is estimated. However, as long as the operation of the other sensor, etc. is controlled in accordance with the result of estimation of the user's body position, the present embodiment may be applied to a case of estimating a state other than the user's respiratory state.

According to at least one of the embodiments described above, a sleep sensor capable of achieving power-saving can be provided.

While certain embodiments have been described, these embodiments have been presented by way of example only, and are not intended to limit the scope of the inventions. Indeed, these embodiments may be embodied in a variety of other forms; furthermore, various omissions, substitutions and changes in the form of the embodiment described herein may be made without departing from the spirit of the invention. The accompanying claims and their equivalents are intended to cover such forms or modifications as would fall within the scope and spirit of the inventions.

What is claimed is:

1. A sleep sensor which is attachable to a user who is sleeping when it is to be used, the sleep sensor detecting snoring for monitoring a respiratory state of the user and comprising:
   a first sensor configured to detect an acceleration signal representing acceleration that acts on the sleep sensor;
   a second sensor configured to detect a signal for estimating the state of the user; and
   a processor configured to:
      estimate the user's body position based on the detected acceleration signal, and
      operate the second sensor when the estimated user's body position is at least one of predefined body positions, wherein:
   the acceleration signal detected by the first sensor includes a direct-current component representing gravitational acceleration that acts on the sleep sensor,
   the second sensor includes a microphone having directivity to a side of an attachment surface of the sleep sensor and configured to detect an intracorporeal sound signal which is generated in accordance with the user's respiratory state as a signal for estimating the user's respiratory state, and
   the processor is further configured to:
      determine whether a direction of the gravitational acceleration agrees with the directivity of the microphone in the estimated user's body position,
      power on the microphone when the direction of the gravitational acceleration agrees with the directivity of the microphone in the estimated user's body position, and
      power off the microphone when the direction of the gravitational acceleration does not agree with the directivity of the microphone.

* * * * *